United States Patent [19]
Takano et al.

[11] Patent Number: 5,254,704
[45] Date of Patent: Oct. 19, 1993

[54] OPTICALLY ACTIVE EPOXIDES AND A PROCESS FOR THE PRODUCTION THEREOF

[75] Inventors: Seiichi Takano; Kunio Ogasawara, both of Sendai, Japan

[73] Assignee: Chisso Corporation, Onaka, Japan

[21] Appl. No.: 885,795

[22] Filed: May 20, 1992

[30] Foreign Application Priority Data

May 20, 1991 [JP] Japan .................... 3-142775

[51] Int. Cl.$^5$ ............... C07D 303/04; C07D 303/14; C07D 301/19
[52] U.S. Cl. ..................... 549/552; 549/529; 549/555; 549/560
[58] Field of Search ................. 549/560, 555, 552

[56] References Cited

U.S. PATENT DOCUMENTS

| | | | |
|---|---|---|---|
| 3,908,016 | 9/1975 | Bowers | 549/555 |
| 4,038,272 | 2/1977 | Partridge et al. | 549/555 |

FOREIGN PATENT DOCUMENTS

83775  6/1980  Japan ................................ 549/560

OTHER PUBLICATIONS

E. J. Corey et al, Leukotriene B. Total Synthesis and Assignment of Stereochemistry, *J. Am. Chem. Soc.* 1980, 102, 7984–7985.

T. Katsuki et al, The First Practical Method for Asymmetric Epoxidation, *J. Am. Chem. Soc.* 1980, 102, 5974–5976.

J. Rokach et al, The Synthesis of Leukotrienes, *SRS-A and Leukotrienes,* Edited by Priscilla J. Piper, 1981, John Wiley & Sons, Ltd. pp. 65–72.

*Primary Examiner*—Joseph E. Evans
*Attorney, Agent, or Firm*—Sheridan Neimark

[57] ABSTRACT

The present invention is optically active epoxides and its production characterized in that the process comprises reacting alkenyl ethylene glycols with 0.5 to 2.0 equivalents of a titanium-tetraalkoxyde, a peroxide and an L−(+)− or D−(−)−dialkyl tartrate at a temperature of −78° to 50° C. to asymmetrically oxidize the alkenyl ethylene glycols. The production of the present invention is an excellent method for producing chiral epoxides in which steric configuration of three asymmetric points can be perfectly controlled, the reaction is performed by mild conditions and the chemical yield and the optical yield are extremely high. The optically active epoxides which can be efficiently produced by the production of the present invention are useful as stating materials of several kinds of compounds.

7 Claims, No Drawings

OPTICALLY ACTIVE EPOXIDES AND A PROCESS FOR THE PRODUCTION THEREOF

BACKGROUND OF THE INVENTION

The present invention related to a process for the production of optically active compounds, characterized in that it comprises oxidizing stereoselectively alkenyl ethyleneglycols, and to the optically active compounds which are advantageously obtained by the method and utilizable as starting materials of physiologically active compounds.

Generally, when the physiologically active compounds having asymmetric carbons, there are plural stereoisomers. Usually, only a stereoisomer among these stereoisomers shows advantageous characteristics. When a stereoisomer which is a racemate or a steroisomer having low optical purity is used, it is apparent that the resulting compounds does not sufficiently exhibit physiological activity.

Optically active compounds which can be produced by the process of the present invention are fully controlled in the steric configuration of three asymmetric positions. Although it is considered that the compounds are useful for raw materials of various useful physiological active compounds, a process for efficiently producing the compounds is still unknown from the complexity of the structure. As an example,

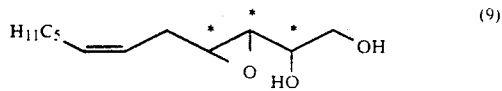

(E. J. Corey et al., J. Am. Chem. Soc. 102 (27), 7984 (1980)) and

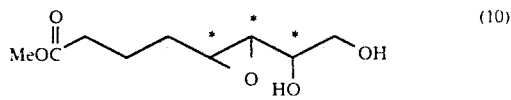

(J. Rokach et al., Prostaglandins, 1, 65 (1981)) are known as intermediates for synthesizing leukotrienes. However, only a process for producing the compounds via several steps from mannose which is a sugar is described, but a process for efficiently producing the compounds is still unknown.

SUMMARY OF THE INVENTION

An object of the present invention is to provide efficiently optically active compounds having high optical purity which are useful for starting materials of physiologically active compounds.

The inventors of the present invention conducted research for attaining the above object, found that particular optically active epoxides having high optical purity are efficiently obtained by oxidation reaction of special alkenyl ethylene glycols used as starting materials, and then brought the present invention to completion.

Namely, the present invention provides a process for the production of an optically active epoxide represented by the general formula:

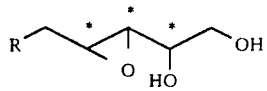

wherein R is a hydrocarbon group of 40 or less carbon atoms and it may contain at least an oxygen, a nitrogen or a sulfur, which comprises reacting an alkenyl ethylene glycol represented by the general formula:

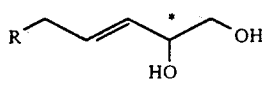

wherein R is the same as that described above, with 0.5 to 2.0 equivalents of a titanium-tetraalkoxyde, a peroxide and an L—(+)— or D—(—)—dialkyl tartrate at a temperature of —78° to 50° C. to asymmetrically oxidize the alkenyl ethylene glycol.

DETAILED DESCRIPTION OF THE INVENTION

In the process, titanium tetraisopropoxide is preferably used as the titanium tetralkoxyde.

Furthermore, t-butylhydroperoxide is preferably used as the peroxide.

Moreover, disopropyl tartrate is preferably used as the dialkyl tartrate.

In addition, the present invention is an optically active epoxide represented by the formula:

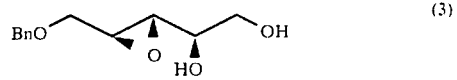

Further, the present invention is an optically active epoxide represented by the formula:

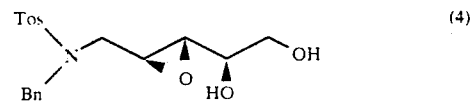

Further, the present invention is an optically active epoxide represented by the formula:

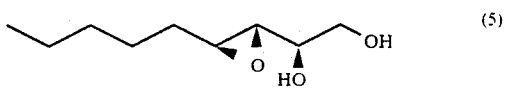

Moreover, the present invention is an optically active epoxide represented by the formula:

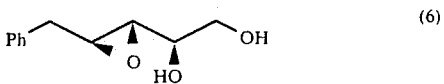

Furthermore, the present invention is an optically active epoxide represented by the formula:

Furthermore, the present invention is an optically active epoxide represented by the formula:

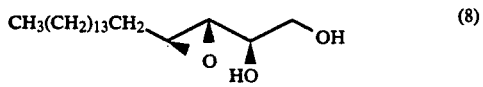
(8)

The following description illustrates the present invention more specifically. The process of the present invention is provided by the following steps.

Namely, an optically active compound represented by the formula (2) is produced by reacting an alkenyl ethyleneglycol represented by the formula (1) with 0.5 to 2.0 equivalent of a titanium tetraalkoxyde, a peroxide and an L—(+)— or D—(—)—dialkyl tartrate at a temperature of −78° to 50° C., preferably −20° C. under anhydrous conditions to asymmetrically oxidize the alkenyl ethyleneglycol. When the amount of the titanium tetraalkoxyde and the like is less than 1.0 equivalent, the chemical yield of the resulting compound is unpreferably too low. When the amount is more than 2.0 equivalent, it is unpreferable because the removal operation of the titanium tetraalkoxide and peroxide becomes troublesome. Further, when the temperature is too low, the reaction hardly proceeds. When the temperature is too high, the steroselectivity unpreferably becomes low.

As the titanium tetraalkoxyde, peroxide and L—(+)— or D—(—)—dialkyl tartrate, industrially available titanium tetraisopropoxide, t-butyl hydroperoxide (abbreviated as TBHP hereinafter), L—(+)— or D—(—)—diisopropyl tartrate (abbreviated as L—(+)— or D—(—)—DIPT hereinafter) can be used without any trouble.

The dehydration from the reaction system is conducted with sufficient efficiency by using molecular sieves. Any kind of dehydrating agents having dehydrating ability can be used. In addition, any kind of nonaqueous solvents can be used in the reaction system. Dichloromethane is particularly preferred.

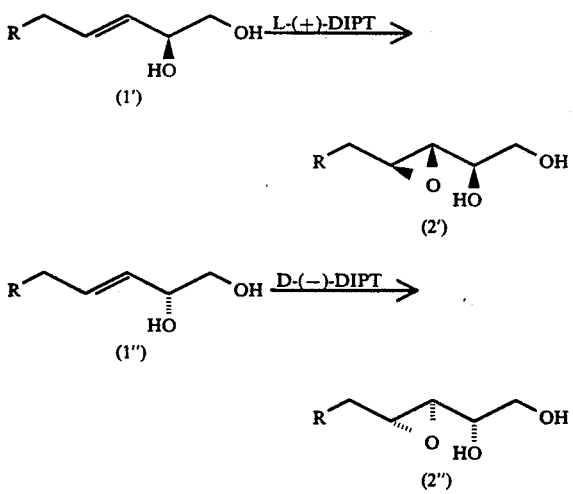

(In the above formula, R is the same as that described above.)

Further, when the compound represented by the formula (1') in the alkenyl ethylene glycol represented by the formula (1) is used as a starting material, the compound represented by the formula (2') can be obtained by using L—(+)—DIPT, while the compound represented by the formula (2") can be obtained by using the formula (1") and D—(—)—DIPT.

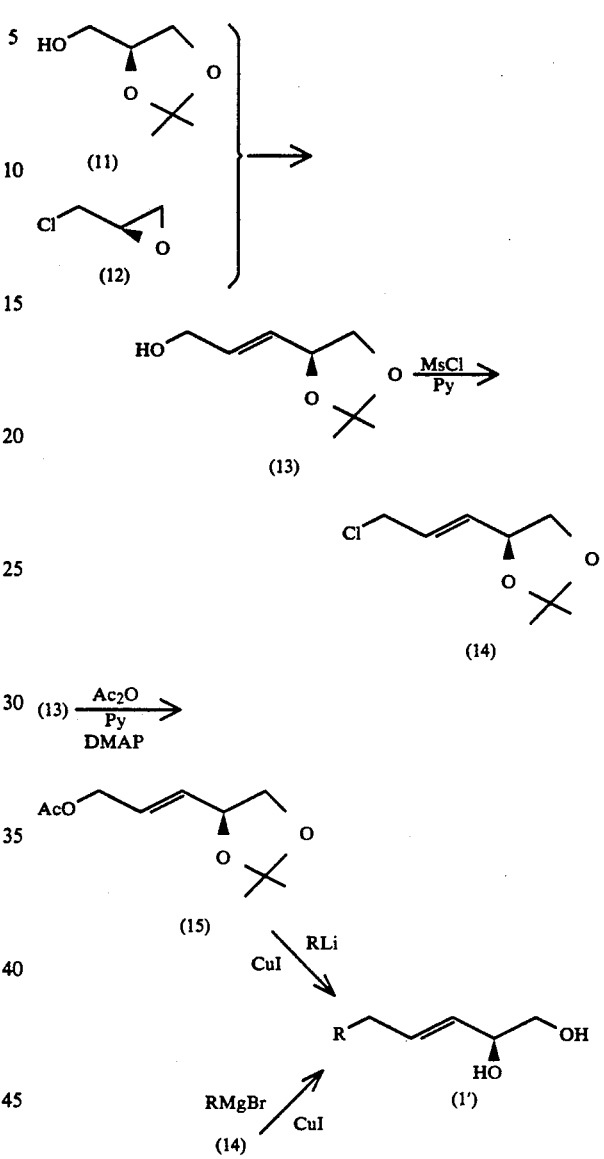

(In the above formula, R is the same as that described above.)

Starting material alkenyl ethylene glycols represented by the formula (1) can be easily produced by using allyl alcohol (13) as a raw material which is easily derived from isopropylidene glycerol (11) or epichlorohydrin (12) industrially available at a low cost. Namely, the compound represented by the formula (14) is produced by chlorinating allyl alcohol represented by the formula (13) with methanesulfonyl chloride in the presence of pyridine, and then the resulting compound is reacted with a Grignard reagent in the present of copper (I) iodide to produce the compound represented by the formula (1').

Further, the compound represented by the formula (15) is produced by acetylating allyl alcohol represented by the formula (13) with acetic anhydride in the presence of pyridine and 4-dimethylaminopyridine (DMAP), and then the resulting compound is reacted with a lithium reagent in the presence of copper (I)

iodide to produce the compound represented by the formula (1'):

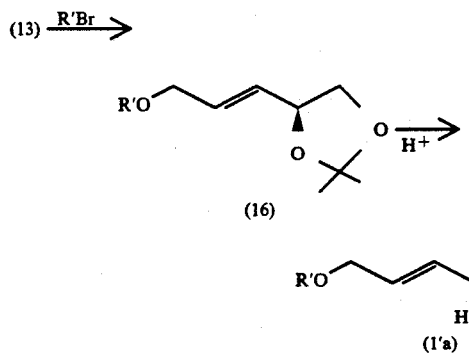

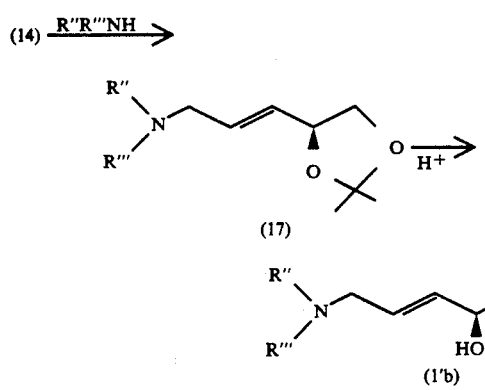

(In the above formula, R', R" and R'" indicates the same or different alkyl groups.)

Then, the compound represented by the formula (16) is obtained by etherifying allyl alcohol represented by the formula (13) with a halide. The resulting compound is treated with an acid to obtain the compound containing oxygens represented by the formula (1'a). Further, the compound represented by the formula (17) is obtained by reacting the compound represented by the formula (14) with an amine, acetone is removing from the resulting compound, and the compound containing a nitrogen atom represented by the formula (1'b) is produced.

Using compounds having opposite configuration to the compounds represented by the formulas (11) and (12) as starting materials, compounds having opposite configuration to the compounds represented by the formulas (1'), (1'a) and (1'b) can be obtained.

The production process of the present invention is applicable to any kind of alkenyl ethyleneglycols. These compounds can be changed to corresponding optically active epoxides represented by the formula (2) having high optical yields and high optical purities. An example is shown in Table 1.

TABLE 1

| Exp. | Compound | Yield (%) | Optical purity (% ee) |
|---|---|---|---|
| 1 | BnO–…–OH (O, OH) | 92 | 89 |
| 2 | Tos,Bn–N–…–OH | 77 | 99 |
| 3 | CH₃(CH₂)₄–…–OH | 73 | 85 |
| 4 | Ph-CH₂–…–OH | 87 | — |
| 5 | CH₂=CH(CH₂)₃–…–OH | 56 | — |
| 6 | CH₃(CH₂)₁₃CH₂–…–OH | 63 | 100 |

DESCRIPTION OF PREFERRED EMBODIMENTS

The following examples illustrate the invention more specifically.

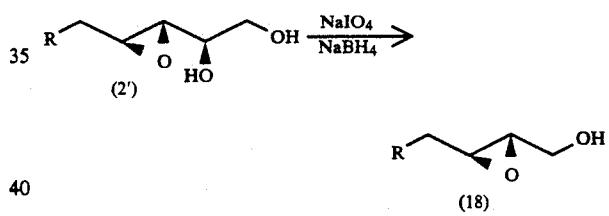

The optical purity of the optically active compound represented by the formula (2') obtained by the process of the present invention is calculated by comparing a reference value of optical purity of a known compound with the specific rotation of epoxyalcohols represented by the formula (18) which is obtained by oxidation with periodic acid followed by reducing with sodium borohydride.

Example 1

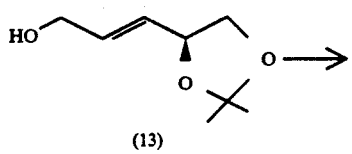

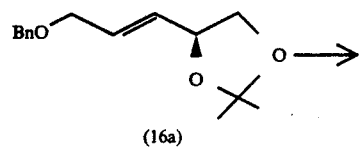

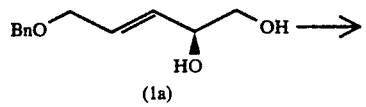

-continued

BnO~~~OH (3), with epoxide O and HO →

BnO~~~OH (18a), with epoxide O →

Production of the optically active epoxide represented by the formula (3) (in the formula (2), a compound wherein R is a benzyloxy group).

(1st step)

To 20 ml of suspension of 1.08 g (22.4 mmol) of sodium hydride in DMF, 3.0 g (18.7 mmol) of allyl alcohol represented by the formula (13) in 3 ml of DMF was added dropwise on ice cooling and the resulting mixture was stirred for 30 min. Then, 2.6 ml (21.5 mmol) of benzyl bromide was added dropwise to the solution and the mixture was further stirred for 8 hours. After adding water, the mixture was extracted with diethyl ether. The organic layer was washed with brine and dried on anhydrous magnesium sulfate and concentrated under reduced pressure. The residue was purified by silica gel chromatography, and 3.28 g (70%) of benzylether represented by the formula (16a) was obtained.

$[\alpha]_D^{28}$ +24.4 (c 2.02, CHCl$_3$)
IR(neat):1454, 1371, 1061 cm$^{-1}$
$^1$H-NMR δ:7.33 (s, 5 H), 6.10–5.50(m, 2 H), 4.52(s, 2 H),
4.65–4.40(m, 1 H), 4.20–3.95(m, 3 H)
3.60(t, 1 H, J=7.8 Hz), 1.43(s, 3 H),
1.40(s, 3 H)
MS m/e:247, 91

(2nd step)

The mixture of 3.2 g (12,8 mmol) of benzylether represented by the formula (16a) obtained in 1st step, 5 ml of 5% hydrochloric acid and 15 ml of methanol was stirred at room temperature for 3 hours. The mixture was neutralized with sodium bicarbonate and concentrated under reduced pressure. The residue was dissolved in dichloromethane. The solution was dried on anhydrous magnesium sulfate and concentrated under reduced pressure. The residue was purified by silica gel chromatography, and 2.55 g (96%) of 4,5-dihydroxy-2-pentenylbenzylether represented by the formula (1a) was obtained.

$[\alpha]_D^{27}$ +4.4°(c 1.34, CHCl$_3$)
IR(neat):3370, 1451, 1067 cm$^{-1}$
$^1$H-NMR δ:7.33 (s, 5 H), 6.10–5.60 (m, 2 H),
4.52(s, 2 H), 4.35–4.10(m, 1 H)
4.00 (brs, 2 H, J=4 Hz), 3.70–3.30 (m, 2 H),
2.65(brs, 2 H)
MS m/e:208, 91

(3rd step)

To 20 ml suspension of 1 g of ground dry molecular sieves 4 A (MS-4 A) in 20 ml of dichloromethane, 0.75 ml (2.52 mmol) of titanium tetraisopropoxide, 675 mg (2.88 mmol) of L—(+)—DIPT in 3 ml of dichloromethane were added at −20° C. The mixture was stirred for 30 minutes. To the mixture, 3 ml of a solution of 500 mg (2.4 mmol) of 4,5-dihydroxy-2-pentenylbenzylether represented by the formula (1a) obtained in (2nd step) in dichloromethane was added. The mixture was stirred for one hour and 1.5 ml (2.64 mmol) of 1.8M-TBHP dichloromethane solution was added dropwise. The mixture was stirred at −20° C. for 80 hours.

To the mixture, 5 ml of water and 25 ml of acetone were added and stirred at room temperature. The mixture was filtered with cerite, and the filtrate was concentrated. The residue was purified by silica gel chromatography and 495 mg (92%) of the optically active epoxide represented by the formula (3) was obtained.

$[\alpha]_D^{25}$ −11.0°(c 1.01, CHCl$_3$)
IR (neat): 3400 cm$^{-1}$
$^1$H-NMR δ:7.33(m, 5 H), 4.56(s, 2 H), 3.80–3.35(m, 5 H),
3.20(m, 1 H), 3.05(brm, 1 H),
2.80(brs, 1 H), 2.50(brs, 1 H)
MS m/e:224, 107.

(4th step)

To the mixture of 100 mg (0.45 mmol) of optically active epoxide of the formula (3) obtained in 3rd step, 1 ml of a saturated aqueous sodium bicarbonate, 1 ml of water and 2 ml of methanol, 210 mg (0.98 mmol) of sodium periodate was added on ice cooling. The mixture was stirred for 3 hours and 37 mg (0.98 mmol) of sodium borohydride was added. The mixture was stirred for 30 minutes and extracted with dichloromethan, and the dichloromethane solution was dried on anhydrous magnesium sulfate and concentrated under reduced pressure. The residue was purified by silica gel chromatography and 58 mg (67%) of the compound represented by the formula (18a) was obtained. The optical purity of the resulting compound was about 89%ee by comparing with specific rotation of reference value.

$[\alpha]_D^{26}$ −18.6°(c 1.6, CHCl$_3$)
(Reference value, $[\alpha]_D^{25}$ −21°(c 0.97, CHCl$_3$)
P. Ma et al., J. Org. Chem., 47, 1378 (1982)).

Example 2

HO~~~ (13), with epoxide O and isopropylidene X, O →

Cl~~~ (14), with epoxide O and isopropylidene X, O →

Tos\N/Bn ~~~OH (1b), with HO →

Tos\N/Bn ~~~OH (4), with epoxide O and HO →

Tos\N/Bn ~~~OH (18b), with epoxide O →

Production of the optically active epoxide represented by the formula (4) (a compound of the formula (2) wherein R is an N-benzyl-p-toluenesulfonamide group).

(1st step)

To the mixture of 3.0 g (19 mmol) of allyl alcohol represented by the formula (13), 2.3 ml (28.5 mmol) of pyridine and 40 ml of dichloromethane, 1.8 ml (22.8 mmol) of methanesulfony chloride was added and stirred at room temperature for 48 hours. The reaction mixture was extracted with dichloromethane and dried on anhydrous magnesium sulfate and concentrated under reduced pressure. The residue was purified by silica gel chromatography and 1.95 g (58%) of a chloride represented by the formula (14) was obtained.

$^1$H-NMR δ:6.15–5.60(m, 2 H), 4.65–4.40(m, 1 H),
4.10(dd, 1 H, J=6.3, 8.3 Hz),
4.05(d, 2 H, J=5.4 Hz),
3.60(dd, 1 H, J=6.9, 6.3 Hz),
1.68(s, 3 H), 1.40(s, 3 H)
MS m/e:177, 161, 43

(2nd step)

500 mg (2.8 mmol) of the chloride represented by the formula (14) obtained in (1st Step) and a solution of 1.2 ml (11.2 mmol) of benzylamine in 5 ml of toluene were stirred for 48 hours at a temperature of 80° C. The solvent was distilled away under reduced pressure. To the residue, 1.2 ml (8.4 mmol) of triethylamine, 20 ml of dichloromethane and 1.33 g (6.0 mmol) of p-toluenesulfonyl chloride were added on ice cooling. The mixture was stirred at room temperature for 10 hours. After the mixture was stirred by adding water and dichloromethane, organic layer was washed with water and dried on anhydrous magnesium sulfate and concentrated under reduced pressure to obtain 2.12 g of crude sulfonamide. A mixture of 2.12 g of the resulting sulfonamide, 3 ml of 5% hydrochloric acid and 10 ml of methanol was stirred at room temperature for 5 hours, and then neutralized by adding sodium hydrogencarbonate. After extracting the reaction mixture with dichloromethane, the extract was dried on anhydrous magnesium sulfate and concentrated under reduced pressure, the residue was purified by silica gel chromatography and 822 mg (78%) of an N-benzyl-p-toluenesulfonamide compound represented by the formula (1b) was obtained.

$[\alpha]_D^{27}$+3.4°(c 1.07, CHCl$_3$)
IR (neat):3400 cm$^{-1}$
$^1$H-NMR δ:7.80–7.60(brd, 2 H, J=8.2 Hz),
7.5–7.20(brm, 7 H), 6.10–5.60(m, 2 H),
4.35(brs, 2 H), 3.90–2.90(m, 7 H),
2.45(brs, 3 H)
MS m/e:343, 91

(3rd Step)

To a suspension of 400 mg of ground dry molecular sieves 4 A(MS-4 A) in 10 ml of dichloromethane, a solution of 0.23 ml (0.76 mmol) of titanium tetraisopropoxide and 205 mg (0.86mmol) of L−(+)−DIPT in 3 ml of dichloromethane were added at −20° C. The mixture was stirred for 30 minutes. A solution of 260 mg (0.72 mmol) of the N-benzyl-p-toluenesulfonamide compound obtained in (2nd Step) in 3 ml of dichloromethane was added to the mixture, and the mixture was stirred for 1 hour. After 0.6 ml (1.08 mmol) of 1.8M-TBHP dichloromethane solution was added dropwise, the mixture was stirred for 72 hours at −20° C. 3 ml of water and 15 ml of acetone were added, and the mixture was stirred at room temperature. After filtrating the mixture with cerite, the filtrate was concentrated. The residue was purified by silica gel chromatography and 210 mg (77%) of the optically active epoxide represented by the fomula (4) was obtained.

$[\alpha]_D^{28}$−22.6°(c 1.01, CHCl$_3$)
IR (neat):3420, 1340, 1155 cm$^{-1}$
$^1$H-NMR δ:7.70(brd, 2 H, J=8.2 Hz), 7.50–7.20(brm, 7 H),
4.35(brs, 2 H), 3.70–3.50(brm, 2 H)
3.50–3.20(m, 1 H), 3.20–3.00(m, 2 H),
3.00–2.80(m, 1 H), 2.70–2.30(m, 3 H),
2.44(brs, 3 H)
MS m/e:378, 346, 222, 91

(4th Step)

To a mixture of 165 mg (0.44 mmol) of the optically active epoxide represented by the formula (4) obtained in (3rd Step), 1 ml of saturated aqueous sodium bicarbonate, 1 ml of water and 2 ml of methanol, 224 mg (1.06 mmol) of sodium periodate was added on ice cooling. After the mixture was stirred for 3 hours, 40 mg (1.06 mmol) of sodium borohydride was added and the mixture was stirred for 30 minutes. The reaction mixture was extracted with dichloromethane and the extract was dried on anhydrous sodium sulfate. The solvent was distilled away under reduced pressure. The residue was purified by silica gel chromatography to obtain 135 mg (88%) of the hydroxy epoxide represented by the formula (18b). It was found that the optical purity of the optically active epoxide represented by the formula (4) was about 99%ee by comparing with a specific rotation of the reference value.

$[\alpha]_D^{27}$−19.9°(c 1.96, CHCl$_3$)
(Reference value, enantiomer $[\alpha]_D^{20}$+20.0°(c 1.84, CHCl$_3$)
C. E. Adams et al., J. Org. Chem., 50, 420 (1985)).

Example 3

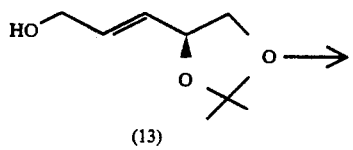

(13)

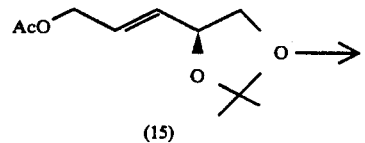

(15)

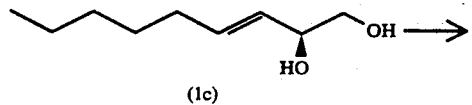

(1c)

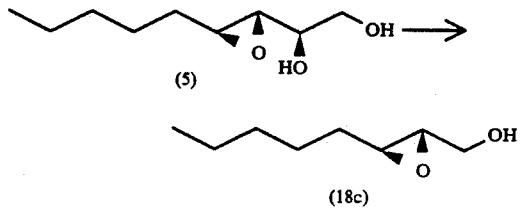

(5)

(18c)

Production of the optically active compound represented by the formula (5) (a compound of the formula (2) wherein R is a n-butyl group)

(1st step)

To a mixture of 700 mg (4.4 mmol) of the allyl alcohol represented by the formula (13), 0.8 ml (9.86 mmol) of pyridine, 109 mg (0.88 mmol) of 4-DMAP and 20 ml of dichloromethane, 0.84 ml (8.9 mmol) of acetic anhydride was added dropwise on ice cooling and the mixture was stirred for 3 hours at a room temperature. The reaction mixture was extracted with dichloromethane, the extract was washed with a saturated aqueous sodium hydrogencarbonate and dried on anhydrous magnesium sulfate, and concentrated under reduced pressure. The residue was purified by silica gel chromatography to obtain 660 mg (75%) of the allyl acetate represented by the formula (15).

IR (neat):1741, 1372 cm$^{-1}$
$^1$H-NMR δ:6.10-5.50(m, 2 H), 4.55(d, 2 H, J=4.4 Hz),
4.60-4.40(m,1 H), 4.10(dd, 1 H, J=6.1, 8.0 Hz), 3.65(t, 1 H, J=8.2 Hz), 2.07(s, 3 H), 1.43(s, 3 H), 1.40(s, 3 H)
MS m/e:201, 185, 43

(2nd step)

To 25 ml of a diethylether solution of 726 mg (3.81 mmol) of copper (I) iodide, 4.8 ml (7.62 mmol) of 1.6M-butyllithium hexane solution was added dropwise, and the mixture was stirred at 0° C. for 15 minutes. After the mixture was cooled to −30° C., a solution of 635 mg (3.18 mmol) of the allyl acetate represented by the formula (15) obtained in (1st Step) in 3 ml of THF was added dropwise, and the mixture was stirred for 1 hour. After a saturated aqueous ammonium chloride was added, the mixture was warmed to room temperature and extracted with diethyl ether. The extract was washed with a saturated aqueous sodium bicarbonate and then with brine. After the extract was dried on anhydrous magnesium sulfate, the solvent was distilled away under reduced pressure and 680 mg of crude acetonide was obtained as the residue. A mixture of 300 mg (1.5 mmol) of the crude acetonide, 2 ml of 5% hydrochloric acid and 5 ml of methanol was stirred at room temperature for 3 hours. After the mixture was neutralized with sodium bicarbonate, it was concentrated under reduced pressure, and the residue was dissolved in dichloromethane. The solution was dried on anhydrous magnesium sulfate and concentrated under reduced pressure. The residue was purified by silica gel chromatography to obtain 156 mg (66%) of 1, 2-dihydroxy-3-nonene represented by the formula (1c).

$[α]_D^{28}$+17.1°(c 1.03, CHCl$_3$)
IR (neat):3360, 1074 cm$^{-1}$
$^1$H-NMR δ:5.80(td, 1 H, J=5.3, 16.0 Hz)
5.45(dd, 1 H, J=5.0, 16.0 Hz),
4.30-4.00(brm, 1 H), 3.70-3.30(m,2 H),
2.45(brs, 2 H), 2.00(brt, 2 H, J=5.5 Hz),
1.50-1.00(brs, 6 H), 0.80(t, 3 H, J=7.3 Hz)
MS m/e:158, 127, 57

(3rd Step)

To a suspension of 600 mg of ground dry molecular sieves 4 A(MS-4a) in 10 ml of dichloromethane, a solution of 0.44 ml (1.20 mmol) of titanium tetraisopropoxide, 395 mg (1.68 mmol) of L−(+)−DIPT in 3 ml of dichloromethane was added at −20° C., and the mixture was stirred for 30 minutes. A solution of 180 mg (1.14 mmol) of 1, 2-dihydroxy-3-nonene represented by the formula (1c) obtained in (2nd Step) in 3 ml of dichloromethane was added to the mixture. After the mixture was stirred for 1 hour, 0.76 ml (1.68 mmol) of 1.8M-TBHP dichlomethane solution was added dropwise, and the mixture was stirred at −20° C. for 72 hours. After adding 2 ml of water and 10 ml of acetone, the mixture was stirred at room temperature. After the mixture was filtered with celite and the filtrate was concentrated. The residue was purified by silica gel chromatography and 145 mg (73%) of the optically active epoxide represented by the formula (5) was obtained.

$[α]_D^{27}$−19.2°(c 1.02, CHCl$_3$)
IR (neat):3350 cm$^{-1}$ $^1$H-NMR δ:3.70(brs, 3 H), 3.20-2.65(m, 4 H),
1.70-1.00(m, 8 H), 0.80(t, 3 H, J=7.5 Hz)
MS m/e:175, 143, 55

(4th Step)

To a mixture of 100 mg (0.57 mmol) of optically active epoxide represented by the formula (5) obtained in (3rd Step), 1 ml of a saturated aqueous sodium bicarbonate, 1 ml of water and 2 ml of methanol, 292 mg (1.36 mmol) of sodium periodate was added on ice cooling. After the mixture was stirred for 3 hours, 73 mg (1.84 mmol) of sodium borohydride was added and the mixture was stirred for 30 minutes. After the reaction mixture was extracted with dichloromethane and the extract was dried on anhydrous sodium sulfate. The solvent was distilled away under reduced pressure. The residue was purified by silica gel chromatography to obtain 70 mg (82%) of 1-hydroxy-2, 3-epoxyoctene (18c). It was found that the optical purity of the optically active epoxide represented by the formula (5) was about 85%ee by comparing with specific rotation of the reference value.

$[α]_D^{27}$−37.9°(c 14, CHCl$_3$)
(Reference value $[α]_D$−44.4°(c 0.49, CHCl$_3$)
( S. Takana et al., J. Chem. Soc, Chem. Commun., 1344 (1989)).

Example 4

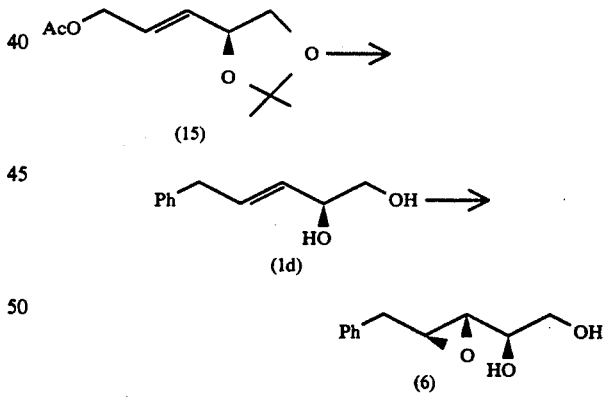

Production of the optically active epoxide represented by the formula (6) (a compound of the formula (2) wherein R is a phenyl group)

(1st step)

To 35 ml of a solution of 3.03 mg (15.9 mmol) of copper (I) iodide in diethyl ether, 16 ml (31.8 mmol) of a 2.0 M-phennyl lithium hexane solution was added dropwise, and the mixture was stirred at 0° C. for 15 minutes. The mixture was cooled to −30° C., 3 ml of a solution of 635 mg (3.18 mmol) of the allyl acetate (15) obtained in example 3 (1st step) in THF was added dropwise and the mixture was stirred for one hour. After adding a saturated aqueous ammonium chloride, the mixture was warmed to a room temperature and extracted with diethyl ether, and the extract was washed with a saturated aqueous sodium bicarbonate and then with brine. The solution was dried on anhydrous magnesium sulfate and concentrated under reduced pressure, and 1.05 g of crude acetonide was obtained as a residue. A mixture of 830 mg of crude acetonide, 2 ml of 5% hydrochloric acid and 5 ml of methanol was stirred at room temperature for 3 hours. The mixture was neutralized with sodium bicarbonate and concentrated under reduced pressure, and the residue was dissolved in dichloromethane. The solution was dried on anhydrous magnesium sulfate, and concentrated under reduced pressure. The residue was purified by silica gel chromatography and 335 mg (74%) of the 1-phenyl-4, 5-dihydroxy-2-pentene represented by the formula (1d) was obtained.

$[\alpha]_D^{27}+9.9°$(c 1.03, CHCl$_3$)
IR (neat):3360 cm$^{-1}$
$^1$H-NMR δ:7.40–710(m, 5 H), 5.95(td, 1 H, J=5.3, 16.0 Hz), 5.50(dd, 1 H, J=5.0, 16.0 hz),
4.30–4.05(m, 1 H), 3.80–3.30(m, 2 H),
3.45(d, 2 H, J=6.6 Hz), 2.20–1.80(m, 2 H)
MS m/e:178, 147, 129

(2nd step)

To a suspension of 800 mg of ground molecular sieves 4 A (MS-4 A) in 15 ml of dichloromethane, a solution of 0.44 ml (1.47 mmol) of titanium tetraisopropoxide, and 395 mg (1.68 mmol) of L−(+)−DIPT in 3 ml of dichloromethane was added, and the mixture was stirred for 30 minutes. After adding a solution of 250 mg (1.4 mmol) of 1-phenyl-4, 5-dihydroxy-2-pentene represented by the formula (1d) obtained in (1st Step) in 3 ml of dichloromethane, the mixture was stirred for one hour, and 1.2 ml (2.1 mmol) of a 1.8M-TBHP dichloromethane solution was added dropwise, and the mixture was stirred at −20° C. for 72 hours. 3 ml of water and 15 ml of acetone were added to the mixture, and the mixture was stirred at room temperature and filtered with cerite, and then the filtrate was concentrated. The residue was purified by silica gel chromatography and 236 mg (87%) of 1-phenyl-4, 5-dihydroxy-2, 3-epoxypentane represented by the formula (6) was obtained.

$[\alpha]_D^{27}-13.3°$(c 1.01, CHCl$_3$)
IR (neat):3460, 1608 cm$^{-1}$
$^1$H-NMR δ:7.40–7.10(m, 5 H), 3.80–3.50(m, 3 H),
3.25–3.18(m, 1 H), 2.95–2.90(m, 1 H),
2.90–2.85(m, 2 H), 2.80(brs, 1 H),
250(brs, 1 H)
MS m/e:194, 163

Example 5

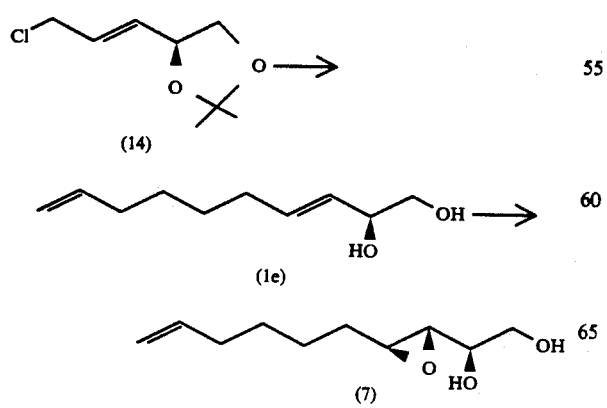

Production of the optically active epoxide represented by the formula (7) (a compound in the formula (2) wherein R is a 1-pentenyl group).

(1st step)

4.8 ml (6.3 mmol) of a solution of 1.32M-pentenyl magnesium bromide in THF was added dropwise to a solution of 600 mg (3.15 mmol) of copper (I) iodide in 10 ml of THF at −30° C. and the mixture was stirred at 0° C. for 15 minutes. The mixture was cooled to −30° C., a solution of 300 mg (2.1 mmol) of the chloride (14) obtained in (1st Step) of Example 2 in 3 ml of THF was added dropwise, and the mixture was stirred for 1 hour. After adding a saturated aqueous ammonium chloride to the mixture, the mixture was warmed to room temperature and extracted with diethyl ether. The extract was washed with a saturated aqueous sodium bicarbonate and with brine. The solution was dried on anhydrous magnesium sulfate and concentrated under reduced pressure to obtain 344 mg (78%) of crude acetonide as a residue. A mixture of 310 mg of crude acetonide, 3 ml of 5% hydrochloric acid and 5 ml of methanol was stirred for 3 hours at room temperature. After neutralizing with sodium bicarbonate, the mixture was concentrated under reduced pressure, and the residue was dissolved in dichloromethane. The solution was dried on anhydrous magnesium sulfate and concentrated under reduced pressure. The residue was purified by silica gel chromatography and 230 mg (92%) of the 1,2-dihydroxy-3,9-decadiene represented by the formula (1e) was obtained.

$[\alpha]_D^{26}+15.4°$(c 1.06, CHCl$_3$)
IR (neat):3340, 1640, 1075 cm$^{-1}$
$^1$H-NMR δ:6.05–4.80(m, 5 H), 4.30–4.00(m, 1 H),
3.75–3.30(m, 2 H), 2.31–1.80(brm, 6 H),
1.50–1.30(brm, 4 H)
MS m/e:169, 139, 57

(2nd Step)

A solution of 0.36 ml (1.20 mmol) of titanium tetraisopropoxide and 320 mg (1.37 mmol) of L−(+)−DIPT in 3 ml of dichloromethane was added to a suspension of 600 mg of ground dry molecular sieves 4 A (MS-4 A) in 15 ml of dichloromethane, and the mixture was stirred for 30 minutes. After adding a solution of 195 mg (1.14 mmol) of 1,2-dihydroxy-3,9-decadiene represented by the formula (1e) obtained in (1st Step) in 3 ml of dichloromethane, the mixture was stirred for 1 hour. 0.96 ml (1.72 mmol) of 1.8M-TBHP dichloromethane solution was added dropwise to the mixture and the mixture was stirred at −20° C. for 72 hours. After adding 3 ml of water and 5 ml of acetone, the mixture was stirred at room temperature and filtered with cerite, and then the filtrate was concentrated. The residue was purified by silica gel chromotography and 116 mg (56%) of 1,2-hydroxy-3,4-epoxy-9-decene represented by the formula (7) was obtained.

$[\alpha]_D^{26}+15.4°$(c 1.06, CHCl$_3$)
IR (neat):3390, 1641 cm$^{-1}$
$^1$H-NMR δ:6.10–5.50(m, 1 H), 5.10–4.80 (m, 2 H),
3.70–3.50(brs, 3 H), 3.40(brs, 1 H),
3.15(brs, 1 H), 3.00–2.70(m,2 H),
2.20–1.90(brm,2 H), 1.70–1.15(brm,6 H),
MS m/e:187, 95, 67

Example 6

(14) [structure: Cl-CH2-CH=CH-CH(-)-CH2CH3 with epoxide-like O and gem-dimethyl]

(1f) CH₃(CH₂)₁₃CH₂—CH=CH—CH(OH)—CH₂—OH with HO (8) CH₃(CH₂)₁₃CH₂—CH(-O-)CH—CH(OH)—CH₂—OH (18f) CH₃(CH₂)₁₃CH₂—CH(-O-)CH—CH₂—OH Production of the optically active epoxide represented by the formula (8) (a compound of the formula (2) wherein R is a tetradecyl group)

(1st Step)

A solution of 11.9 ml (8.31 mmol) of 0.7M-tetradecyl magnesium bromide in THF was added dropwise to a solution of 791 mg (4.15 mmol) of copper (I) iodide in 15 ml of THF, and the mixture was stirred at 0° C. for 15 minutes. The mixture was cooled to −30° C. A solution of 400 mg (2.77 mmol) of the chloride represented by the formula (14) obtained in (1st Step) of Example 2 in 3 ml of THF was added dropwsie to the mixture, the mixture was stirred for 1 hour. After adding a saturated aqueous ammonium chloride, the mixture was warmed to room temperature and extracted with diethyl ether. The extract was washed with a saturated aqueous sodium bicarbonate and with brine. The solution was dried on anhydrous magnesium sulfate, and concentrated under reduced pressure. The residue was purified by silica gel chromatography and 490 mg (88%) of the dihydroxy compound represented by the formula (1f) was obtained.

$[\alpha]_D^{27}+9.2°$(c 1.03, CHCl₃)

¹H-NMR δ:5.85(td, 1 H, J=5.4, 16.0 Hz), 5.45(dd, 1 H, J=5.0, 16.0 Hz), 4.40–4.10(m, 1 H), 3.85–3.30(m, 2 H), 2.10–1.80(m, 4 H), 1.70–1.20(brm, 4 H), 1.26(brs, 22 H), 0.80(brt, 3 H, J=7.3 Hz).

(2nd Step)

To a suspension of 800 mg of ground dry molecular sieves 4a (MS-4a) in 30 ml of dichloromethane, a solution of 0.47 ml (1.58 mmol) of titanium tetra isopropoxide, 408 mg (1.73 mmol) of L−(+)−DIPT in 3 ml of dichloromethane was added at −20° C., and the mixture was stirred for 30 minutes. A solution of 330 mg (1.44 mmol) of the dihydroxy compound represented by the formula (1f) obtained in (1st Step) was added to the mixture, the mixture was stirred for 1 hour. After 0.96 ml (1.73 mmol) of 1.8M-TBHP dichloromethane solution was added dropwise, the mixture was stirred at −20° C. for 72 hours. After adding 3 ml of water and 15 ml of acetone, the mixture was stirred at room temperature and filtered with cerite, and then the filtrate was concentrated. The residue was purified by silica gel chromatography and 223 mg (63%) of the dihydroxy epoxide represented by the formula (8) was obtained.

$[\alpha]_D^{28}-20°$(c 0.98, CHCl₃)

IR (neat):3340 cm⁻¹

¹H-NMRδ:3.70(brs, 3 H), 3.20–2.65(brm, 5 H), 1.70–1.20(brm,4 H), 1.26(brs, 26 Hz), 0.80(brt, 3 H,J=7.3 Hz)

MS m/e:282, 267, 57.

(3rd Step)

To a mixture of 140 mg (0.57 mmol) of the dihydroxyepoxide represented by the formula (8) obtained in (2nd Step), 1 ml of a saturated aqueous sodium bicarbonate, 1 ml of water, 2 ml of methanol and 2 ml of THF, on ice cooling 246 mg (1.14 mmol) of sodium periodide was added. After the mixture was stirred for 3 hours, 65 mg (1.71 mmol) of sodium borohydride was added, and the mixture was stirred for 30 minutes. The reaction mixture was extracted with dichloromethane, and the extract was dried on anhydrous sodium sulfate and concentrated under reduced pressure. The residue was purified by silica gel chromatography and 110 mg (91%) of the hydroxyepoxide represented by the formula (18f) was obtained. The analytical results of ¹H-NMR were agreed very closely with those of reference values. Further, compared with the optical rotation of reference value, it was found that the hydroxyepoxide represented by the formula (18f) was substantially optically pure.

$[\alpha]_D^{26}-22.5°$(c 1.00, CHCl₃)

(Reference value, enantiomer $[\alpha]_D^{23}+22.5°$(c 0.79, CHCl₃)

W. R. Roush et at., J. Org. Chem., 50, 3752(1985)).

The process of the present invention is an excellent method for producing chiral epoxides, by which the steric configuration of three asymmetric positions can be fully controlled. Further, the reaction can be conducted under mild conditions, and the chemical yields and optical yields are very high. In addition, since the substrate specificity is low, as shown in Table 1 as embodiments, substrates having several constitutions can be used as starting materials to produce corresponding chiral epoxides.

Further, according to the process of the present invention, it is possible to produce the optically active epoxide represented by the formula (22) having high optical purity. The above intermediate represented by the formula (9) for synthesizing leukotriene can be obtained by the reduction of the resulting compound (22) with a Lindlar catalyst.

(22) C₅H₁₁—C≡C—CH₂—CH(-O-)CH—CH(OH)—CH₂—OH  →Lindlar cat.→

(9) C₅H₁₁—CH=CH—CH₂—CH(-O-)CH—CH(OH)—CH₂—OH

Similarly, the compound represented by the formula (23) which is obtained by the process of the present invention can be introduced to the intermediate represented by said formula (10) for synthesizing leukotriene via steps of hydroboration and oxidation reactions.

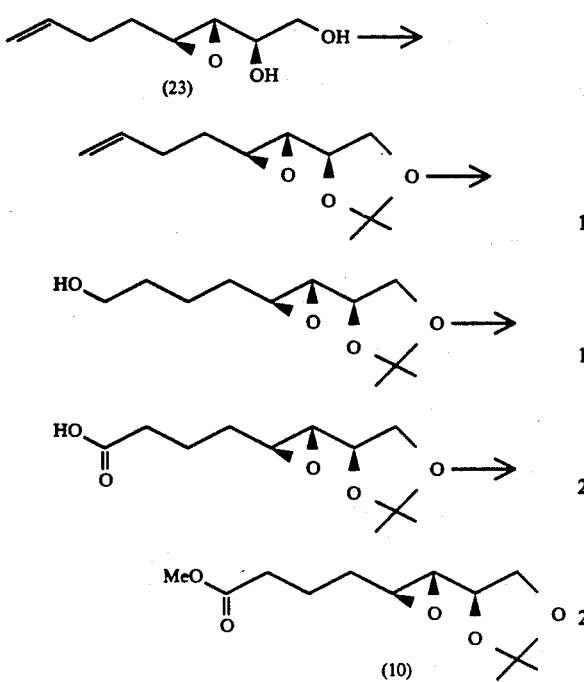

Moreover, optically active compounds which can be efficiently produced by the process of the present invention are available as starting materials of several kind of useful compounds.

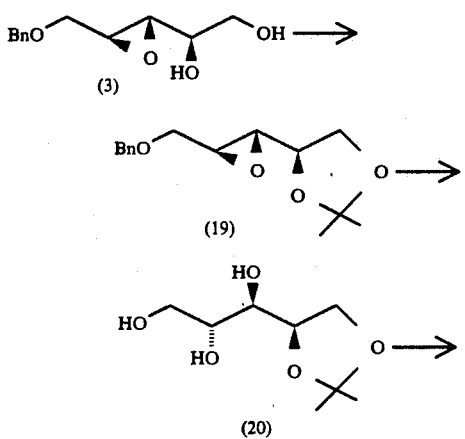

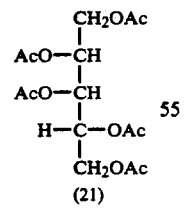

For example, from compound of Example 1, the compound represented by the formula (20) from which D-arabinitol is induced by a known reaction, is induced by a process of protection of two hydroxy groups, epoxide ring opening and debenzylation. (T. Katsuki et al., J. Org. Chem., 47, 1371 (1982)).

Moreover, by using a compound having a steric configuration different from that of the compound represented by the formula (3), corresponding several kind of saccharides, ribitol and xylitol can be prepared instead of the compound represented by the formula (21).

We claim:

1. An optically active epoxide represented by the general formula:

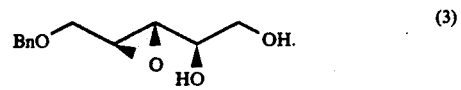

2. An optically active epoxide represented by the general formula:

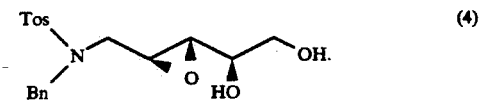

3. An optically active epoxide represented by the general formula:

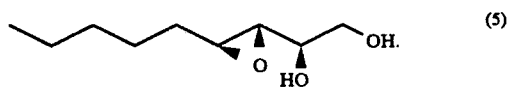

4. An optically active epoxide represented by the general formula:

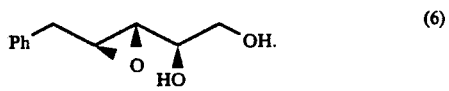

5. An optically active epoxide represented by the general formula:

6. An optically active epoxide represented by the general formula:

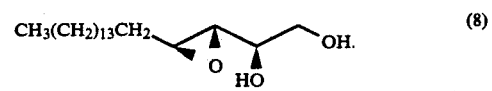

7. An optically active epoxide of high optical purity having the formula:

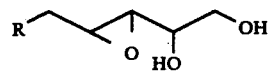

wherein R is selected from the group consisting of BnO,

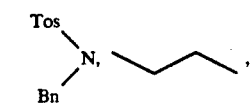

and $CH_3(CH_2)_{13}$.

* * * * *

UNITED STATES PATENT AND TRADEMARK OFFICE
CERTIFICATE OF CORRECTION

PATENT NO. : 5,254,704
DATED : October 19, 1993
INVENTOR(S) : Seiichi Takano, et al.

It is certified that error appears in the above-indentified patent and that said Letters Patent is hereby corrected as shown below:

ON THE TITLE PAGE ITEM [73] delete " Chisso Corporation, Onaka, Japan" and insert therefor -- Chisso Corporation, Osaka, Japan--

Signed and Sealed this

Eighteenth Day of October, 1994

Attest:

BRUCE LEHMAN

*Attesting Officer*     *Commissioner of Patents and Trademarks*